United States Patent [19]

Kumoi et al.

[11] Patent Number: 4,625,064
[45] Date of Patent: Nov. 25, 1986

[54] METHOD FOR PRODUCING BIS [β(N,N-DIMETHYLAMINO)ETHYL]ETHER

[75] Inventors: Sadakatsu Kumoi, Hikari; Keiji Mitarai, Shinnanyo; Yukihiro Tsutsumi, Tokuyama, all of Japan

[73] Assignee: Toyo Soda Manufacturing Co., Ltd., Shinnanyo, Japan

[21] Appl. No.: 597,312

[22] Filed: Apr. 6, 1984

[30] Foreign Application Priority Data

Apr. 7, 1983 [JP] Japan .................................. 58-60076

[51] Int. Cl.$^4$ ............................................. C07C 93/04
[52] U.S. Cl. .................... 564/486; 564/295; 564/296; 564/468; 564/511
[58] Field of Search .................... 564/511, 468, 486

[56] References Cited

U.S. PATENT DOCUMENTS 3,400,157 9/1968 Poppelsdorf ........................ 564/486
3,426,072 2/1969 Warner .............................. 564/508

*Primary Examiner*—Floyd D. Higel
*Attorney, Agent, or Firm*—Armstrong, Nikaido, Marmelstein & Kubovcik

[57] ABSTRACT

An improved process for preparing a bis [β-(N,N-dimethylamino)ethyl]ether by reacting a bismethohalide of bis [β-(N,N-dimethylamino)ethyl]ether represented by the following general formula:

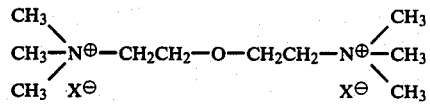

(wherein X denotes a halogen atom), with an aliphatic amine having a boiling point of not lower than 220° C. at atmospheric pressure and having a primary amino group in the molecule thereof. The process comprises the following two steps (a) and (b): (a) a step of distilling out water at a temperature of not more than 130° C. under reduced pressure from a mixture of said bismethohalide aqueous solution and said aliphatic amine to provide a concentration of said bismethohalide to water of not less than 85% by weight, and (b) a step of reacting said bismethohalide and amine in a solid-liquid phase at a temperature of not lower than 140° C.

6 Claims, No Drawings

METHOD FOR PRODUCING BIS [β(N,N-DIMETHYLAMINO)ETHYL]ETHER

DETAILED DESCRIPTION OF THE INVENTION

The present invention relates to an improved method for producing bis[β-(N,N-dimethylamino)ethyl]ether.

It is known that bis[β-(N,N-dimethylamino)ethyl]ether is a compound useful as a catalyst for producing a polyurethane.

It is known to produce a tertiary amine compound by reacting various kinds of neucleophilic reagents with a quarternary ammonium salt compound (14 III 1398 of New Experimental Chemistry Lecture, 1978). Likewise, a method for producing a corresponding bis[β-(N,N-dimethylamino)ethyl]ether (hereinafter abbreviated as "etheramine") by a demethylation reaction of a bismethohalide of bis[β-(N,N-dimethylamino)ethyl]ether (hereinafter abbreviated as "bismethohalide") is disclosed in U.S. Pat. No. 3,400,157 and Japanese Publication No. Sho 48-7411 (U.S. Pat. No. 3,426,072). In U.S. Pat. No. 3,400,157, a bismethochloride aqueous solution of bis[β-(N,N-dimethylamino)ethyl]ether obtained by the reaction of dichloroethylether with a 40% trimethylamine aqueous solution undergoes a demethylation reaction to provide said corresponding etheramine in a 67% yield. This yield is not considered to be high.

In Japanese Publication No. Sho 48-7411 (corresponding to U.S. Pat. No. 3,426,072), a 71% aqueous solution of said bismethochloride and a polyamine having a boiling point of more than 220° C., such as aminoethylethanolanine, triethylenetetramine and the like, undergo a reaction at ordinary pressure or reduced pressure to provide the etheramine in a yield of 71% at the highest.

The method using these high boiling point polyamines is improved in some operations for separating and recovering the ethoramino and the used polyamines from the reaction mixtures and thus can be said to be an excellent process from aspect of operations, but it is not yet satisfactory from the standpoint of yield. In order that this process employing a dihaloethylether as a starting material, which is comparatively expensive, in particular, may become an industrial process which is excellent from an economical standpoint, further improvements in of etheramine yield are strongly desired.

Upon reviewing these circumstances, the inventors of this invention have found that the etheramine can be produced in a surprisingly high yield by selecting a reaction mode of a heterogeneous system consisting of a solid-liquid mixed phase in which the reaction temperature and the quantity of water in the reaction mixture are controlled to particular conditions at the time of reacting the bismethohalide with an amine compound having boiling point, at atmospheric pressure, of not lower than 220° C. and having a primary amino group.

That is, the present invention provides a method for producing bis[β-(N,N-dimethylamino)ethyl]ether wherein an aqueous solution of a bismethohalide compound of bis[β-(N,N-dimethylamino)ethyl]ether represented by the following general formula:

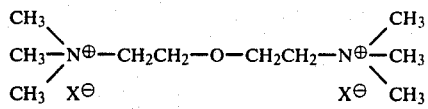

(X denotes a halogen atom) is reacted with an aliphatic amine having boiling point, at atmospheric pressure, of not lower than 220° C. and having a primary amino group in the molecule thereof, the process being characterized in comprising the two steps of: (a) distilling out water at a temperature of not more than 130° C. from a reaction mixture of said bismethohalide aqueous solution and said aliphatic amine to provide a concentration of said bismethohalide to water of not lower than 85% by weight, and (b) performing a heterogeneous, solid-liquid phase, reaction at a temperature of not lower than 140° C. The starting bismethohalide used in this invention is represented by the following general formula:

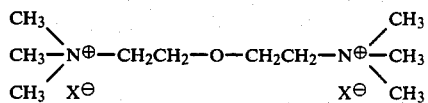

(X denotes a halogen atom). Generally, a bismethohalide of bis[β-(N,N-dimethylamino)ethyl]ether in which X denotes chlorine, bromine or the like, that is, the bismethochloride of bis[β-(N,N-dimethylamino)ethyl]ether or the bismethobromide of bis[β-(N,N-dimethylamino)ethyl]ether is used as the starting material, on account of economics, convenience of obtaining the starting material and so on.

These bismethohalides can be obtained as a homogeneous aqueous solution thereof by reacting a dihaloethylether which is industrially obtainable with trimethylamine aqueous solution. The solubility of the bismethohalide in water varies with temperature, but it is nearly about 71% by weight in a temperature range of 20°–100° C., and so a homogeneous aqueous solution of the bismethohalide of below the above concentration is usually available. In other words, a homogeneous aqueous solution of the bismethohalide is used as the starting material, which is obtained by reacting dihaloethylether with trimethylamine aqueous solution.

The aliphatic amine employed in this invention is an aliphatic amine compound having a boiling point of not below 220° C. at atmospheric pressure and having a primary amino group in the molecule thereof. This aliphatic amine can contain a secondary amino group, a tertiary amino group, oxy group or hydroxy group in the molecule thereof, besides the primary amino group which gives rise to no particular restriction.

As typical aliphatic amines, there are exemplified polyethylenepolyamines such as triethylenetetramine, tetraethylenepentamine, pentaethylenehexamine and the like (these polyethylenepolyamines usually consist of a mixture of several kinds of ethyleneamines containing piperazine ring); polypropylenepolyamines such as dipropylenetriamine, tripropylenetetramine, tetrapropylenepentamine and the like; high boiling point polyamines such as N,N'-bis(3-aminopropyl)ethylenediamino, N-aminoethylethanolamine, N-aminoethylpropanolamine and the like.

The reaction process in this invention comprises two steps. The first step is heating of the reaction mixture of the starting bismethohalide aqueous solution and the high boiling point aliphatic amine at a temperature of not above 130° C., preferably not above 120° C., thereby distilling and removing water out of the reaction mixture under ordinary pressure or reduced pressure to concentrate it to a concentration of the bismethohalide to water of not below 85% by weight, preferably not below 90% by weight. The second step is heating of the resultant heterogeneous reaction mixture, in which a part of the bismethohalide deposits and disperses in the high boiling point aliphatic amine, at a temperature of not below 140° C., preferably not below 160° C., to produce the resultant etheramine.

The addition amount of the high boiling point aliphatic amine is usually not lower than 2 mols to 1 mol of the bismethahalide. The high boiling point aliphatic amine functions also as a dispersing agent of the bismethohalide. The dispersing property of the bismethohalide is not improved, which causes a decrease of the yield of the etheramine, when at least 2 mols, preferably not lower than 3 mols, are not added. The upper limit of the amount of the high boiling point aliphatic amine is not restricted and an effective amount thereof can be selected on considering production efficiency of the reactor, recovery amount of the used amine and so forth.

In the operation of the first step for concentrating the reaction mixture with dehydration until a concentration of the bismethohalide to water reaches not lower than 85% by weight it is important in that the operation is performed at a temperature of not more than 130° C., preferably not more than 120° C.

In case the above dehydration operation is carried out at a temperature beyond 130° C., there is a remarkable decrease in the yield, which means an extreme disadvantage economically. The reaction mixture should be concentrated with dehydration at a temperature of not more than 130° C. until a concentration of the bismothehalide to water reaches, preferably, 90% by weight, which causes further improvement in the yield of the etheramine, and hence is more advantageous. The operation of removing water with distillation as above can usually be performed under ordinary pressure or reduced pressure. Performing the step under reduced pressure renders effective dehydration feasible, which is preferable. The dehydration is usually completed in 0.5-10 hours under a pressure of 1-750 mmHg. A dehydration operation of 0.5-5 hours under 50-300 mmHg, which is preferable, provides a more effective operation and further can cause a favorable effect on the yield of the etheramine. The reaction mixture obtained by performing the first step operation is a heterogeneous reaction mixture consisting of a solid-liquid phase in which a part of the bismethohalide is deposited and dispersed mainly into the high boiling point aliphatic amine.

The reaction in the second step is featured by heating the above reaction mixture at a temperature of not lower than 140° C., preferably not lower than 160° C., to perform a heterogeneous reaction.

The reaction of the bismethohalide with the high boiling point aliphatic amine can proceed usually even at 140° C., but the reaction rate is so slow that it can not be said to be effective from an industrial aspect, because it belongs to the heterogeneous reaction.

Therefore, it is preferable to perform the heterogeneous reaction at a temperature of not lower than 160° C., which can produce the desired etheramine with high efficiency. Generally speaking, the heterogeneous reaction, in which contact of solid and liquid are not usually sufficient, can not be said to be advantageous from the aspect of reaction rate. On the contrary, the method of producing the etheramine by this invention can provide the etheramine with a surprisingly high yield, which hence becomes extremely advantageous from an industrial aspect.

The heterogeneous reaction can be carried out under ordinary pressure, reduced pressure or increased pressure, and there is no particular restriction in the reaction pressure. In the reaction under ordinary pressure or reduced pressure, the reaction can be carried out with distillation of the resultant etheramine out of the reaction mixture. On the other hand, in the reaction under increased pressure, the etheramine can be recovered by distillation from a resulting homogeneous solution after the reaction is completed.

In order to produce said etheramine industrially, it is necessary to increase the economical efficiency of the process by repeatedly using the aliphatic amine in the reaction. That is, after the reaction, an alkali compound is added to the reaction mixture comprising a hydrochloric acid salt of the amine to liberate the amine, which is recovered.

As to the alkali compound used for the neutralization, there is no restriction in particular, and a hydroxide, carbonate and the like of an alkali metal can be exemplified. Usually, sodium hydroxide or potassium hydroxide can be used as a solution thereof, and the addition amount thereof is not less than twice the number of moles of the starting bismethohalide, i.e., 2.0-2.2 times moles equivalent. After the neutralization, the aliphatic amine and said etheramine can be recovered through ordinary distillation, filtration, extraction and other separating means. The recovered aliphatic amine can be used in the next reaction repeatedly. The repeated using of the aliphatic amine as a demethylation agent increases the resulting amount of the etheramine per unit weight of the amine to elevate the economical efficiency of the process remarkably.

As stated above, in the case of reacting the starting bismethohalide with the high boiling point amine, the etheramine is produced with high efficiency which surpasses the conventional technique and makes it feasible to perform the heterogeneous reaction consisting of a solid-liquid phase, by selecting the reaction processes proposed by this invention. This invention is further explained hereinafter by examples, which do not provide this invention with any restriction.

EXAMPLE 1

Preparation of bismethochloride of bis[$\beta$-(N,N-dimethylamino)ethyl]ether

Into an autoclave having inside volume of 5 liters equipped with a magnetic stirrer, 2,820 g of 30% trimethylamine aqueous solution (846 g of trimethylamine) and 860 g of bis($\beta$-chloroethyl)ether were introduced and heated at 70° C. for 6 hours. After the reaction, unreacted trimethylamine was purged out, and the reaction mixture was analysed. As a result of quanitative analysis of chlorine ion by Volhard method, it was 12.0 equivalents (theoretical value being 12.02 equivalents).

Through $^1$H-NMR and $^{13}$C-NMR analysis of the reaction mixture, it was identified that the product was bismethochloride of bis[$\beta$-(N,N-dimethylamino)ethyl]ether and that it was produced nearly quantitatively. The total weight of the remained reaction mixture after the unreacted trimethylamine was purged was 3,530 g, and the concentration of the bismethochloride of bis[β-(N,N-dimethylamino)ethyl]ether therein was 44.5% by weight.

Preparation of bis[β-(N,N-dimethylamino)ethyl]ether

Into a glass four-necked flask equipped with a stirrer, thermometer, dropping funnel and short column for distillation of length 30 cm (filled with glass Rashig rings), 292 g of triethylenetetramine was added and heated at 120° C. From the dropping funnel, 587 g of an aqueous solution having a concentration of 44.5% by weight of bismethochloride of bis[β-(N,N-dimethylamino)ethyl]ether (hereinafter referred to as the bismethochloride) (261.2 g of the bismethochloride and 325.8 g of water) was added thereinto, and the inside temperature thereof was maintained at 105° C. While keeping the inside pressure at 110 mmHg, water was distilled away. At the time 310 g of water was distilled away (the concentration of the bismethochloride to water in the reaction mixture was 94%), the temperature of the reaction mixture which formed a heterogeneous solid-liquid phase was raised from 105° C. to 170° C. The reaction was carried out for 3.5 hours in a region of substantial reaction temperature of 140° C. to 170° C. A distillate, 164.9 g, was obtained at a temperature of the column top of 100°-130° C. (110 mmHg). As a result of gas-chromatographic analysis of this distillate, 140.2 g of bis[β-(N,N-dimethylamino)ethyl]-ether (hereinafter referred to as the etheramine) was identified. The yield of the etheramine was 87%.

EXAMPLE 2

In the same glass four-necked flask as in Example 1, 472 g of tetraethylenepentamine was added and heated at 110° C. From the dropping funnel, 587 g of 44.5% aqueous solution of bis[β-(N,N-dimethylamino)ethyl]ether was added thereinto (which contained 261.2 g of the bismethochloride), the inside temperature was kept at 115° C. While maintaining the inside pressure 140 mmHg, a distillate, 297 g, was obtained at a temperature of the column top of 45°-80° C. As a result of gas-chromatographic analysis thereof, the distillate was determined to be water.

In the reaction mixture consisting of a solid-liquid phase after 297 g of water was distilled away, the concentration of the bismethochloride to water was 90%.

The temperature of reaction mixture was raised from 115° C. to 175° C., and the reaction was carried out at a region of substantial reaction temperature of 140° C. to 175° C. for 4 hours. A distillate, 170 g, was obtained at a column top temperature of 110°-135° C. (140 mmHg). As a result of gas-chromatographic analysis of this distillate, it could be identified that 142.6 g of the etheramine was present. The yield of the etheramine was 88.5%.

EXAMPLE 3

Into a stainless autoclave of a magnetic stirrer type, 429 g of triethylenetetramine and 587 g of 44.5% aqueous solution of bismethochloride of bis[β-(N,N-dimethylamino)ethyl]ether (which contained 261.2 g of the bismethochloride) were added, and heated at 90°-100° C. With maintaining the inside pressure at 150°-170 mmHg, 300 g of water was distilled away through a glass short column installed in a valve on the upper cover of the autoclave over a period of 1 hour. After 300 g of water was distilled away, the concentration of the bismethochloride to water in the reaction mixture was 91%. After entirely closing the valve of the autoclave and elevating the inside temperature up to 177° C. under the gauge pressure of 1-3 kg/cm², the reaction was carried out for 2.5 hours. After completion of the reacton, the total amount of the reaction mixture was transferred to the glass four-necked flask used in Example 1 and was subjected to a crude distillation to give 145 g of a distillate at a column top temperature of 115°-132° C. (140 mmHg). As a result of gas-chromatographic analysis of this distillate, it was identified that 138.6 g of the etheramine was present. The yield of etheramine was 86%.

COMPARATIVE EXAMPLE 1

Into the same glass four-necked flask as used in Example 1, 402 g of triethylenetetramine was added and heated at 150° C. From a dropping funnel, 587 g of a 44.5% aqueous solution of bismethochloride of bis[β-(N,N-dimethylamino)ethyl]ether (which contained 261.2 g of the bismethochloride) was added thereinto, and the inside temperature thereof was kept at 150° C. While maintaining the inside pressure at 170 mmHg, water and the reaction product were distilled out. At column top temperatures of 65°-130° C. and more than 130° C., 346 g of a distillate and 134 g of another distillate were obtained, respectively. As a result of gas-chromatographic analysis of each distillate, it was identified that 109.5 g of the etheramine was formed. The yield of the etheramine was 68%.

What is claimed is:

1. A method for producing bis[β-(N,N-dimethylamino)-ethyl]ether comprising:
   (a) providing a mixture of an aqueous solution of a bismethohalide of bis[β-(N,N-dimethylamino)ethyl]ether represented by the formula:

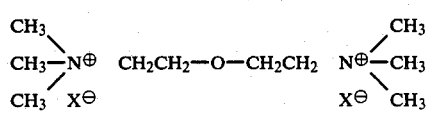

where X is a halogen atom, and a component choosen from the group consisting of polyethylene polyamines, polypropylene polyamines or high boiling point polyamines, all having a boiling point not below 220° C. at atmospheric pressure and having a primary amino group in the molecule thereof;
   (b) distilling said mixture at a temperature of 120° C. or less under reduced pressure to remove water from the mixture and increase the concentration of said bismethohalide to water to not lower than 85% by weight and to form a heterogeneous mixture consisting of a solid-liquid phase n which a part of said bismethohalide is dispersed in said polyamine;
   (c) reacting the bismethohalide and polyamine in said heterogeneous mixture at a temperature of not lower than 140° C. to form said bis[β-(N,N-dimethylamino)ethyl]ether; and
   (d) recovering the bis[β-(N,N-dimethylaminoethyl]ether.

2. The method of claim 1, wherein the aliphatic amine is selected from polyethylenepolyamines.

3. The method of claim 1, wherein the aliphatic amine is employed in an amount of not less than 2 moles per 1 mol of the bismethohalide.

4. The method of claim 1, wherein the step of removing water from the reaction mixture with distillation thereof is carried out under 1–750 mmHg.

5. The method of claim 1 wherein the aqueous solution of bismethohalide is an aqueous solution produced by reacting a dihaloethylether with an aqueous solution of a trimethylamine.

6. The method of claim 1, wherein the polyamines is selected from a group consisting of triethylenetetramine, tetraethylenepentamine, pentaethylenehexamine, dipropylenetriamine, tripropylenetetramine and bis(3-aminopropyl)-ethylenediamine.

* * * * *